United States Patent
Wang et al.

(10) Patent No.: US 12,403,167 B2
(45) Date of Patent: Sep. 2, 2025

(54) **PHENYLETHANOID GLYCOSIDE EXTRACT FROM *ACANTHUS ILICIFOLIUS* L., PREPARATION METHOD THEREOF AND USE AS ANTI-LIVER INJURY MEDICAMENT**

(71) Applicant: OCEAN UNIVERSITY OF CHINA, Shandong (CN)

(72) Inventors: Changyun Wang, Shandong (CN); Changlun Shao, Shandong (CN); Mengqi Zhang, Shandong (CN); Hong Bai, Shandong (CN); Xia Ren, Shandong (CN); Shijun Yue, Shandong (CN); Lanting Xin, Shandong (CN); Qing Zhao, Shandong (CN)

(73) Assignee: OCEAN UNIVERSITY OF CHINA, Shandong (CN)

( * ) Notice: Subject to any disclaimer, the term of this patent is extended or adjusted under 35 U.S.C. 154(b) by 796 days.

(21) Appl. No.: 17/485,995

(22) Filed: Sep. 27, 2021

(65) Prior Publication Data
US 2022/0031783 A1   Feb. 3, 2022

Related U.S. Application Data

(63) Continuation-in-part of application No. PCT/CN2020/096097, filed on Jun. 15, 2020.

(30) Foreign Application Priority Data

Dec. 12, 2019  (CN) .......................... 201911272041.5

(51) Int. Cl.
| | |
|---|---|
| A61K 36/19 | (2006.01) |
| A61K 31/192 | (2006.01) |
| A61K 31/7032 | (2006.01) |
| A61P 1/16 | (2006.01) |

(52) U.S. Cl.
CPC ............ *A61K 36/19* (2013.01); *A61K 31/192* (2013.01); *A61K 31/7032* (2013.01); *A61P 1/16* (2018.01); *A61K 2236/15* (2013.01); *A61K 2236/17* (2013.01); *A61K 2236/333* (2013.01); *A61K 2236/51* (2013.01)

(58) Field of Classification Search
None
See application file for complete search history.

(56) References Cited

U.S. PATENT DOCUMENTS

| | | | |
|---|---|---|---|
| 7,087,252 B2 * | 8/2006 | Tu ........................... | A61K 36/64 424/725 |
| 2015/0087606 A1 * | 3/2015 | Lin .......................... | A61P 27/02 514/25 |
| 2016/0256507 A1 * | 9/2016 | Lo Franco ............. | A61K 36/63 |

FOREIGN PATENT DOCUMENTS

| | | |
|---|---|---|
| CN | 102670631 A | 9/2012 |
| CN | 103285053 A | 9/2013 |
| CN | 110812375 A | 2/2020 |

OTHER PUBLICATIONS

Rajamanickam et al., "Chemopreventive Effect of Acanthus ilicifolius Extract on Modulating Antioxidants, Lipid Peroxidation and Membrane Bound Enzymes in Diethyl Nitrosamine Induced Liver Carcinogenesis", International Journal of Cancer Research, 12(1), pp. 1-16 (Year: 2016).*

(Continued)

*Primary Examiner* — Bethany P Barham
*Assistant Examiner* — Peter Anthopolos
(74) *Attorney, Agent, or Firm* — LEASON ELLIS LLP

(57) ABSTRACT

Provided are a phenylethanoid glycoside extract from the plant *A. ilicifolius* L., a preparation method thereof, and its use as an anti-liver injury medicament. The preparation method of the phenylethanoid glycoside extract comprises following steps: pulverizing dried whole plant *Acanthus ilicifolius* L. and passing through 20-30 mesh sieve to obtain *Acanthus ilicifolius* L. powder, adding 50%-95% ethanol solution whose mass is 8-20 times of the powder, soaking and extracting under reflux, filtering and collecting extract of the powder, and extracting a filter residue under reflux with 50%-95% ethanol solution whose mass is 8-10 times of the filter residue and collecting extract of the filter residue, combining, concentrating and subjecting to macroporous resin column chromatography, eluting successively by 10%, 30% and 50% ethanol solutions for four column volumes, respectively, collecting fraction eluted by the 50% ethanol solution and drying to obtain the phenylethanoid glycoside extract.

12 Claims, 2 Drawing Sheets

(56) References Cited

OTHER PUBLICATIONS

Zhang et al., Hepatoprotective effects of total phenylethanoid glycosides from *Acanthus ilicifolius* L. against carbon tetrachloride-induced hepatotoxicity, Journal of Ethnopharmacology, vol. 256, Mar. 26, 2020 (Mar. 26, 2020).

Zhang et al., Simultaneous Quantification of Four Phenylethanoid Glycosides in Rat Plasma by UPLC-MS/MS and Its Application to a Pharmacokinetic Study of Acanthus Ilicifolius Herb, Molecules, 2019, vol. 24, No. 17: 3117.

Wu et al., New aliphatic alcohol and (Z)-4-coumaric acid glycosides from Acanthus ilicifolius, Chem. Pharm.Bull., vol. 51, No. 10, 2003: 1201-1203.

International Search Report of PCT/CN2020/096097, mailed on Sep. 8, 2020.

Cao et al. "Preparation Technology of Verbascoside and Isoverbascoside from Pedicularis Kansuensis", Chinese Traditional and Herbal Drugs, vol. 47, No. 10, 2016, pp. 1696-1701. 6 pages.

Zhao et al. "Advances in Research of Pharmacological Activity of Phenylethanoid Glycosides in Cistanche", Asia-Pacific Traditional Medicine, vol. 9, No. 5, 2013, pp. 77-79. Abstract. 2 pages.

International Search Report and Written Opinion of PCT/CN2020/096097, mailed on Sep. 8, 2020.

\* cited by examiner

PHENYLETHANOID GLYCOSIDE EXTRACT FROM ACANTHUS ILICIFOLIUS L., PREPARATION METHOD THEREOF AND USE AS ANTI-LIVER INJURY MEDICAMENT

CROSS-REFERENCE TO RELATED APPLICATIONS

The present application is a continuation-in-part application based on International Patent Application No. PCT/CN2020/096097, which claims priority to Chinese Patent Application No. 201911272041.5, filed with the China National Intellectual Property Administration (CNIPA) on Dec. 12, 2019, and entitled "Phenylethanoid glycoside extract from Acanthus ilicifolius L., preparation method thereof and use as anti-liver injury medicament", all of which are incorporated herein by reference in their entireties.

TECHNICAL FIELD

The present disclosure belongs to the technical field of medical product research and development, and specifically relates to a phenylethanoid glycoside extract from Acanthus ilicifolius L. (A. ilicifolius L.), preparation method thereof and use as anti-liver injury medicament.

BACKGROUND ART

Hepatitis is one of the most common liver diseases. It has been reported that acute or chronic inflammation caused by various pathogenic factors (such as viruses, bacteria, parasites, chemicals, medicaments, alcohol and other hepatotoxic agents) is the main cause of severe hepatocellular damage. Liver damage is accompanied by dysfunction of metabolism and synthesis, leading to liver fibrosis, cirrhosis, and even liver cancer. The current medicaments used to treat liver diseases such as steroids, vaccines and antiviral medicaments have limited therapeutic effects and are accompanied by serious side effects. Therefore, the research and development of anti-liver injury medicaments has always been a hot spot in the development of medicaments for the treatment of liver diseases.

The plant A. ilicifolius L., which belongs to the family Acanthaceae, is one of the coastal mangrove species distributed in the tropical and subtropical intertidal habitats. At present, there are no related patent reports on the application of phenylethanoid glycosides from A. ilicifolius L. for anti-liver injury.

SUMMARY OF THE INVENTION

The present disclosure provides a phenylethanoid glycoside extract from A. ilicifolius L. as a total effective part and use thereof in the field of anti-liver injury.

The present disclosure provides a phenylethanoid glycoside extract, wherein the phenylethanoid glycoside extract was prepared by a method comprising following steps:
pulverizing dried whole plant Acanthus ilicifolius L. and passing through a 20-30 mesh sieve to obtain Acanthus ilicifolius L. powder, adding a 50%-95% ethanol solution whose mass is 8-20 times of the powder, soaking for 1-3 h and then extracting under reflux for 2-4 h, filtering and collecting an extract of the powder, and then extracting a filter residue under reflux for 1.5-2 h with 50%-95% ethanol solution whose mass is 8-10 times of the filter residue and collecting an extract of the filter residue, combining the extract of the powder and the extract of the filter residue, concentrating and subjecting to macroporous resin column chromatography, eluting successively by 10%, 30% and 50% ethanol solutions for four column volumes, respectively, collecting a fraction eluted by the 50% ethanol solution and drying to obtain the phenylethanoid glycoside extract, wherein the percentages of ethanol solutions are all volume percentage.

As for the macroporous resin column chromatography, the stationary phase employs D101 type or AB-8 type macroporous resin is preferably employed as a stationary phase.

A content of the phenylethanoid glycoside compounds in the phenylethanoid glycoside extract is more than 70 wt %.

Optionally, the content of the phenylethanoid glycoside compounds in the phenylethanoid glycoside extract is 73.78±2.00 wt %.

The phenylethanoid glycoside extract comprises at least four compounds of acteoside, isocrenatoside, isoacteoside and p-coumaric acid, wherein the contents of acteoside, isocrenatoside, isoacteoside and p-coumaric acid is 52.33%, 4.32%, 6.89% and 7.45%, respectively.

An HPLC profile of the phenylethanoid glycoside extract is substantially consistent with FIG. 2. HPLC conditions are as follows: chromatography column: reversed phase Kromasil $C_{18}$ preparative column (250×4.6 mm, 5.0 μm) used under 30° C. Gradient elution (solvent A: methanol; solvent B: 0.1% formic acid in water): 0-5 min, 5-5% (methanol); 5-30 min, 5-25% (methanol); 30-40 min, 25-60% (methanol); 40-50 min, 60-95% (methanol). Injection volume: 10 μL. Flow rate: 1.0 mL/min. Detection wavelength: 332 nm.

Another embodiment of the present disclosure provides a preparation method of the phenylethanoid glycoside extract, characterized by comprising following steps:
pulverizing dried whole plant Acanthus ilicifolius L. and passing through a 20-30 mesh sieve to obtain Acanthus ilicifolius L. powder, adding a 50%-95% ethanol solution whose mass is 8-20 times of the powder, soaking for 1-3 h and then extracting under reflux for 2-4 h, filtering and collecting an extract of the powder, and then extracting a filter residue under reflux for 1.5-2 h with 50%-95% ethanol solution whose mass is 8-10 times of the filter residue and collecting an extract of the filter residue, combining the extract of the powder and the extract of the filter residue, concentrating and subjecting to macroporous resin column chromatography, eluting successively by 10%, 30% and 50% ethanol solutions for four column volumes, respectively, collecting a fraction eluted by the 50% ethanol solution and drying to obtain the phenylethanoid glycoside extract, wherein the percentages of ethanol solutions are all volume percentage.

As for the macroporous resin column chromatography, the stationary phase is preferably D101 type or AB-8 type macroporous resin.

Another embodiment of the present disclosure provides use of the phenylethanoid glycoside extract in preparation of medicaments for treating and/or preventing liver injury.

Another embodiment of the present disclosure provides use of the phenylethanoid glycoside extract in preparation of medicaments that increase superoxide dismutase (SOD) activity and reduce malondialdehyde (MDA) levels.

Another embodiment of the present disclosure provides use of the phenylethanoid glycoside extract in the preparation of medicaments for reducing alanine aminotransferase (ALT) and aspartate aminotransferase (AST) levels in serum.

Another embodiment of the present disclosure provides use of the phenylethanoid glycoside extract in the preparation of medicaments for inhibiting inflammation in liver tissue.

Another embodiment of the present disclosure provides a method for increasing SOD activity in a subject by administering an effective dose of the phenylethanoid glycoside extract to the subject.

Another embodiment of the present disclosure provides a method for reducing a level of lipid peroxide malondialdehyde (MDA) in a subject by administering an effective dose of the phenylethanoid glycoside extract to the subject.

The percentages of the ethanol solutions described in the present disclosure are all volume percentages.

Compared with the prior art, the present application discloses the use of phenylethanoid glycoside extract from *A. ilicifolius* L. in anti-liver injury use for the first time. The preparation method of phenylethanoid glycoside extract from *A. ilicifolius* L. in the present disclosure is simple, and easy to operate, with high production efficiency. The anti-liver injury effect of the phenylethanoid glycoside extract from *A. ilicifolius* L. is significant, and which could restore normal biochemical indexes in the mouse serum and liver tissue, ameliorate the liver diseases of the mice, and increase the survival rates of liver cells in vitro. The present disclosure provides a new direction for the prevention and treatment of liver injury.

DETAILED DESCRIPTION OF THE EMBODIMENTS

In order to facilitate a further understanding of the present disclosure, the embodiments provide below illustrate in more detail. However, these examples are only for a better understanding of the disclosure and shall not be construed as limiting the scope of the present disclosure or implementation principles of the present disclosure, and the embodiments of the present disclosure are not limited to the following content.

Example 1

Preparation and identification of phenylethanoid glycoside extract.

1. Preparation of Phenylethanoid Glycoside Extract

The crude powder of the plant was obtained after the dried whole plant of *A. ilicifolius* L. was smashed and passed through a 20-30 mesh sieve. The 95% ethanol solution (10 L) was added to the powder of 1 kg. After being soaked for 2 h and refluxed for 3 h, the extract of the powder was collected. Then the filter residue was refluxed and extracted for another 1.5 h with 95% ethanol solution (8 L). The two extracts were combined, concentrated and subjected to D101 macroporous resin column chromatography, eluted successively by 10%, 30% and 50% ethanol solutions for 4 column volumes, respectively. The fraction eluted with 50% ethanol solution was collected and dried to obtain the phenylethanoid glycoside extract.

2. Identification of Phenylethanoid Glycosides in the Extract

Figure 1:
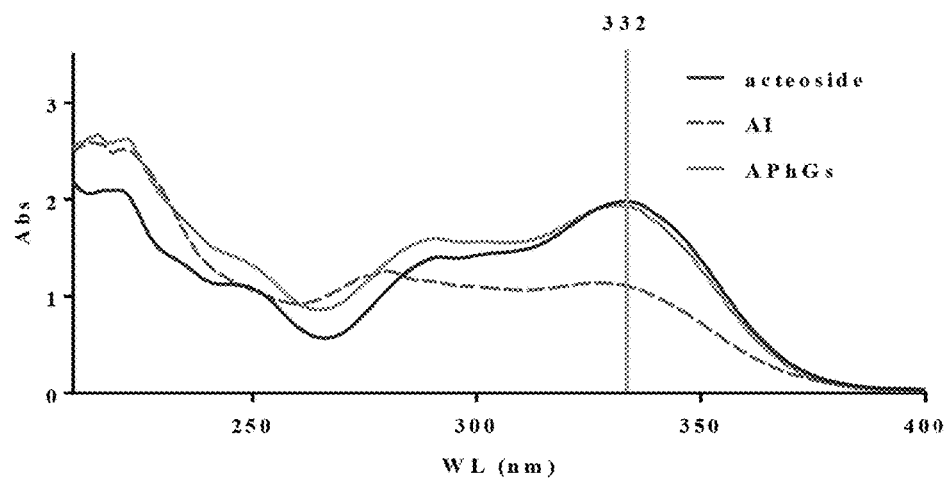
FIG. 1. Ultraviolet scanning spectra of 50% ethanol eluate (APhGs), acteoside and alcohol extract of *A. ilicifolius* L. (AI).

The characteristic of the ultraviolet spectrum of phenylethanoid glycoside is the maximum absorption at 332 nm. Therefore, each elution fraction was scanned at 200-400 nm ultraviolet wavelength, and the scanned spectrum of each eluted fraction was compared with that of the representative compound acteoside. The spectrophotometric method was also used to determine the phenylethanoid glycoside content. The results showed that the 50% ethanol eluate had similar scanned spectrum with acteoside, with the largest UV absorption value at 332 nm (FIG. 1), indicating that the main components of this eluate were phenylethanoid glycosides. The standard curve was drawn with the content of acteoside (mg/mL) as the abscissa (X) and the absorbance as the ordinate (Y) measured at the wavelength of 332 nm. The regression equation of acteoside was Y=58.36X+0.2279 ($R^2$=0.9919). According to this equation, the content of phenylethanoid glycosides in the 50% ethanol component was 73.78% converted to acteoside. The 50% ethanol eluted fraction was used in the following anti-liver injury experiment.

Figure 2:
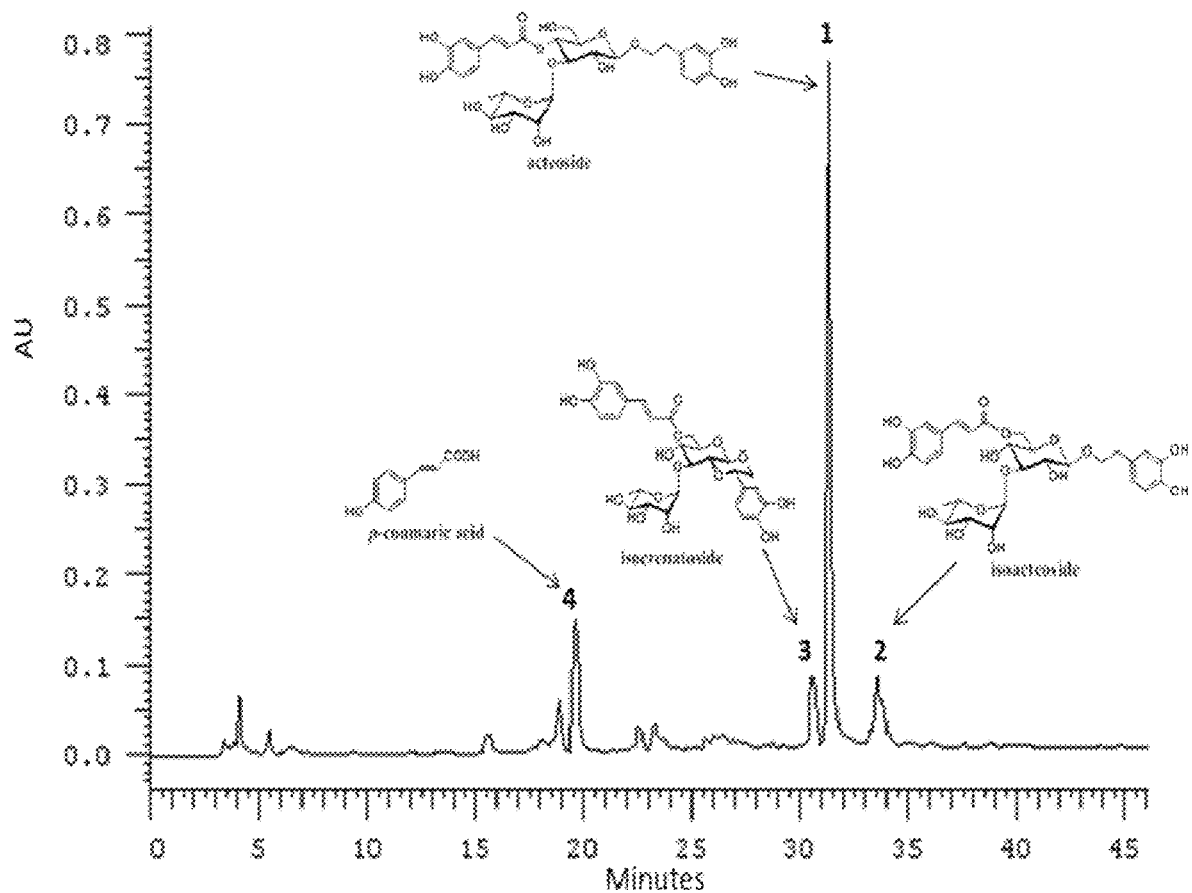
FIG. 2. HPLC fingerprint of the phenylethanoid glycoside components ($\lambda$=332 nm). Column model: Kromasil $C_{18}$ preparative HPLC column (250×4.6 mm, 5 μm). Gradient elution: methanol-water system, 0-5 min, 5-5% (methanol); 5-30 min, 5-25% (methanol); 30-40 min, 25-60% (methanol); 40-50 min, 60-95% (methanol). Injection volume: 10 μL.
Figure 3A:
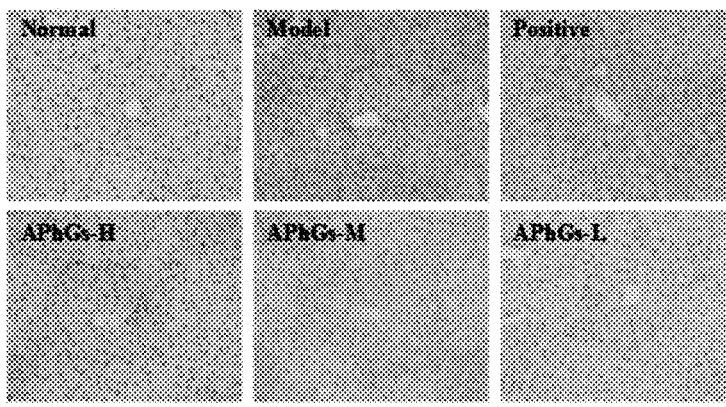
FIG. 3A: TNF-α immunohistochemistry results for the liver tissue of each group of experimental mice (200×)
Figure 3B:
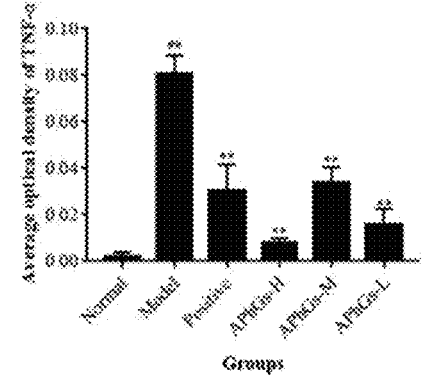
FIG. 3B: average optical density of TNF-α.
Figure 3C:
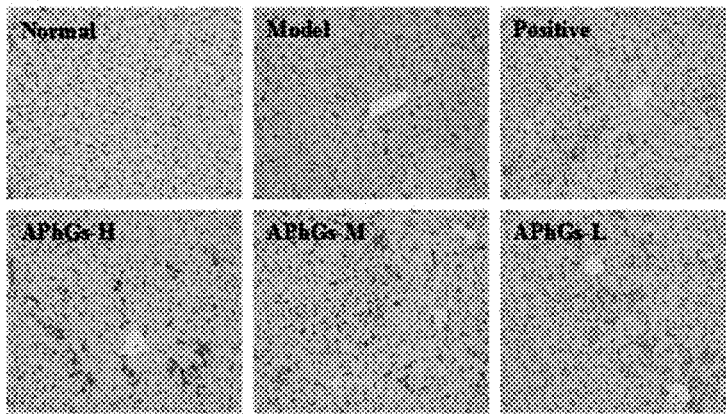
FIG. 3C: IL-1β immunohistochemistry results for the liver tissue of each group of experimental mice (200×)
Figure 3D:
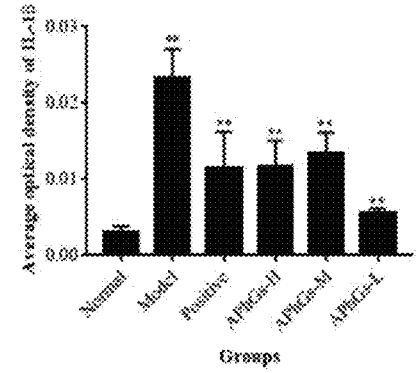
FIG. 3D: average optical density of IL-1β (compared with the normal group ##P<0.01; compared with the model group *P<0.05, **P<0.01).

The main compounds of the phenylethanoid glycoside extract from *A. ilicifolius* L. were determined by comparing with known compounds (standards acteoside, isoacteoside, isocrenatoside, and p-coumaric acid isolated and identified in *A. ilicifolius* L.) and the HPLC fingerprint characteristics (retention time, UV absorption characteristics) of the phenylethanoid glycoside extract. The results have shown that the phenylethanoid glycoside extract from *A. ilicifolius* L. mainly comprise three phenylethanoid glycoside compounds, and one phenolic acid compound (FIG. 2).

Example 2

Pharmacodynamics of phenylethanoid glycoside extract from *A. ilicifolius* L. on $CCl_4$-induced mouse liver injury model in vivo.

1. Experimental Methods

Forty eight C57 mice (20-22 g) of both genders were supplied by the Experimental Animal Center of Hubei Province, China (NO. 42000600033017). The above 48 mice were randomly divided into 6 groups (8 mice each group), and the phenylethanoid glycoside extract of the present disclosure (the phenylethanoid glycoside group, APhGs) were intraperitoneally injected with the doses of 300 mg/kg (high dose group), 150 mg/kg (medium dose group), and 75 mg/kg (low dose group). The positive group was given silybin (150 mg/kg), and the normal group, as well as model group was given normal saline. All groups were treated as above once/d for 3 consecutive days. Two hours after the last administration, the normal group was intraperitoneally injected with 15 μL of olive oil/mouse, and the other groups were intraperitoneally injected with 15 μL of 50% $CCl_4$ (diluted with olive oil 1:1)/mouse. Eight hours later, all the mice were anesthetized. Then blood was collected by cardiac puncture, and liver tissue was collected for testing biochemical indexes and making pathological sections.

1.1 Serum Biochemical Indexes

The detection of alanine aminotransferase (ALT) and aspartate aminotransferase (AST) of serum samples from each group mice were conducted according to the instructions of ELISA kit for ALT and AST. The absorbances (OD values) of serum ALT and AST at 450 nm were obtained by a microplate reader. The ALT and AST enzyme activities were calculated based on the OD values.

The detection of superoxide dismutase (SOD) and malondialdehyde (MDA) of serum samples from each group of mice were conducted according to the instructions of ELISA kit for SOD and MDA. The OD values of serum SOD at 550 nm and MDA at 532 nm were obtained by a microplate reader, respectively. The SOD and MDA enzyme activities were calculated based on the OD values.

1.2 Biochemical Indexes of Liver Tissue Homogenate

The detection of SOD and MDA of liver homogenate samples from each group mice were conducted according to the instructions of ELISA kit for SOD and MDA. The OD values of liver SOD at 550 nm and MDA at 532 nm were obtained by a microplate reader, respectively. The SOD and MDA enzyme activities were calculated based on the OD values.

1.3 Pathological Observation of Liver

Fresh liver tissue was fixed with fixative for 24 h. After alcohol dehydration, the embedded sections were treated with paraffin, stained with H&E staining solution, and the liver tissue structure and changes thereof were observed with a microscope.

1.4 Immunohistochemistry Experiment

Immunohistochemical analysis was performed using deparaffinized liver sections. The sections were immersed in distilled water at room temperature for 25 minutes, and blocked with 3% rabbit serum for 30 minutes. Then TNF-α or IL-1β antibody was added, followed by incubation overnight at 4° C. After washing with PBS, the sections were treated with HRP-labeled rabbit anti-goat immunoglobulin for 50 minutes at room temperature. Then, the sections were immersed in PBS for 5 minutes, and then stained with DAB and hematoxylin. The processed sections were inspected under microscope, and the images were acquired and analyzed.

1.5 Data Processing and Statistical Methods

Immunohistochemical analysis software: Image-pro plus 6.0 (Media Cybernetics, Inc., Rockville, MD, USA); experimental data statistical software: GraphPad Prism 7. The results were represented by mean values ±standard deviation ($\bar{x}\pm s$). The difference $P<0.05$ meant statistically significant.

2 Results 2.1 the Effect of Phenylethanoid Glycoside Extract from *A. ilicifolius* L. On Serum ALT, AST, SOD and MDA in $CCl_4$-Induced Liver Injury Mice Compared with the normal group, the ALT and AST activities in the serum of the $CCl_4$ model group were significantly increased ($P<0.01$) (Table 1). Compared with the model group, the ALT and AST levels of the APhGs groups were reduced. Especially, the ALT and AST activities of the APhGs-H group were 931.53±132.04 and 802.66±105.12 U/L ($P<0.05$), respectively, much lower than the model group (ALT=1299.08±178.40, AST=1068.55±196.59 U/L), indicating that phenylethanoid glycoside extract can significantly reduce the activities of mouse serum ALT and AST.

The serum SOD activity in the model group decreased to 661.36±62.37 U/mL (normal group: 849.58±65.18 U/mL) (Table 1). Compared with the model group, the administration of phenylethanoid glycoside extract could significantly increase the SOD activity. The activities of the phenylethanoid glycoside extract in the high, middle and low dose groups were 834.81±72.44, 796.351±35.13 and 858.84±32.05 U/mL ($P<0.05$), respectively. These results indicated that phenylethanoid glycoside extract could significantly prevent the decrease in oxidase activity induced by $CCl_4$.

The serum MDA level of the model group was significantly increased to 14.64±2.40 μM (normal group: 7.29±0.91 μM) (Table 1). The high and medium doses of phenylethanoid glycoside extract can reduce MDA levels to 12.30±2.08 and 12.69±3.19 μM, respectively. These results indicated that phenylethanoid glycoside extract could prevent the increase in the level of lipid peroxidation products induced by $CCl_4$.

TABLE 1

Effects of APhGs on the activities of serum ALT, AST and SOD, and level of MDA in the $CCl_4$-induced acute liver injury mice (n = 8, $\bar{x} \pm s$).

| Groups | Dose | ALT (U/L) | AST (U/L) | SOD (U/mL) | MDA (uM) |
|---|---|---|---|---|---|
| Normal group | — | 69.14 ± 16.20 | 163.53 ± 23.37 | 849.58 ± 65.18 | 7.29 ± 0.91 |
| Model group | — | 1299.08 ± 178.40## | 1068.55 ± 196.59## | 661.36 ± 62.37# | 14.64 ± 2.40# |
| Positive group | 150 mg/kg | 736.27 ± 112.27** | 776.68 ± 102.23* | 743.47 ± 87.88 | 8.32 ± 1.91* |
| APhGs-H group | 300 mg/Kg | 931.53 ± 132.04* | 802.66 ± 105.12* | 834.81 ± 72.44* | 12.30 ± 2.08 |
| APhGs-M group | 150 mg/Kg | 1112.55 ± 178.44 | 945.78 ± 128.69 | 796.35 ± 135.13 | 12.69 ± 3.19 |
| APhGs-L group | 75 mg/Kg | 1208.49 ± 214.69 | 947.60 ± 182.99 | 858.84 ± 32.05* | 14.71 ± 1.04 |

Statistically significant differences #P < 0.05 and ##P < 0.01, respectively, compared with the normal group; statistically significant differences *P < 0.05 and **P < 0.01, respectively, compared with the model group.

2.2 The effect of APhGs on SOD and MDA in liver tissue of $CCl_4$-induced liver injury mice Compared with the normal group, the SOD activity in the liver tissue of the model group was reduced (Table 2). APhGs could significantly increase SOD activity ($P<0.01$, $P<0.05$). In particular, the SOD activities of the APhGs-H and APhGs-M groups were better than that of the silybin group. The MDA level of the model group increased significantly (Table 2). APhGs groups could reduce MDA level ($P<0.05$). These results indicated that phenylethanoid glycoside extract could prevent the decrease of oxidase activity and the increase of lipid peroxidation product levels induced by $CCl_4$.

TABLE 2

Effects of APhGs on SOD activity and MDA level in the liver tissue of $CCl_4$-induced acute liver injury mice (n = 8, $\bar{x} \pm s$).

| Groups | Dose | SOD (U/mg prot) | MDA (nmol/mg prot) |
|---|---|---|---|
| Normal group | — | 646.18 ± 62.5 | 0.31 ± 0.06 |
| Model group | — | 443.17 ± 40.12[##] | 0.80 ± 0.19[##] |
| Positive group | 150 mg/kg | 610.91 ± 81.06* | 0.56 ± 0.08* |
| APhGs-H group | 300 mg/Kg | 674.30 ± 94.11* | 0.65 ± 0.06* |
| APhGs-M group | 150 mg/Kg | 669.01 ± 23.71** | 0.69 ± 0.07* |
| APhGs-L group | 75 mg/Kg | 610.74 ± 23.31** | 0.70 ± 0.05* |

Statistically significant differences [##]$P < 0.01$, compared with the normal group; statistically significant differences *$P < 0.05$, **$P < 0.01$, respectively, compared with the model group.

2.3 Immunohistochemical staining results

The immunohistochemical results of APhGs on TNF-α protein in liver tissue of mice induced by $CCl_4$ were shown in FIG. 3 (A and B). TNF-α in the $CCl_4$ model group was expressed more in the cytoplasm. The TNF-α expression levels of mice in the APhGs groups were all decreased, especially that in APhGs-H group. The average optical density analysis also confirmed this result.

The immunohistochemical results of APhGs on IL-1β protein in liver tissue of mice induced by $CCl_4$ were shown in FIG. 3 (C and D). IL-1β in the $CCl_4$ model group was expressed more in the cytoplasm. The expression levels of IL-1β in the mice of APhGs groups were all decreased. The average optical density analysis also confirmed this result. The above immunohistochemical results showed that phenylethanoid glycoside extract could inhibit the inflammatory response of liver tissue induced by $CCl_4$.

2.4 H.E. Staining Results of Liver Tissue

Figure 4A:
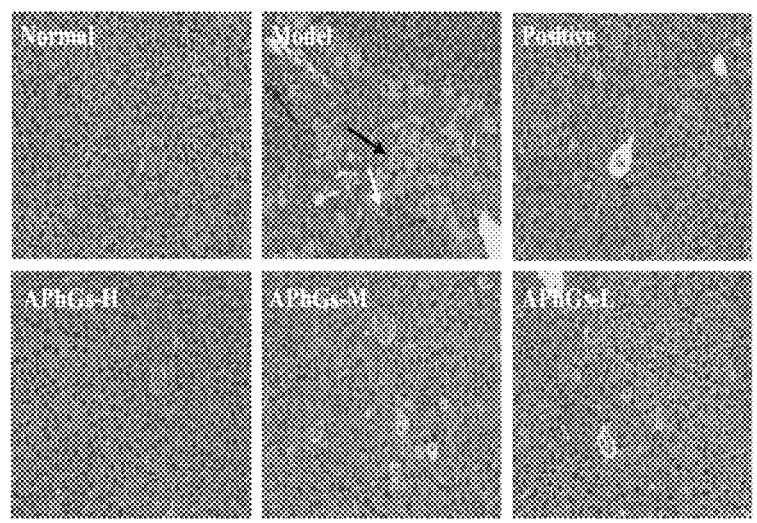
FIG. 4A is the liver tissue pathological section of each group of experimental mice (200×)
Figure 4B:
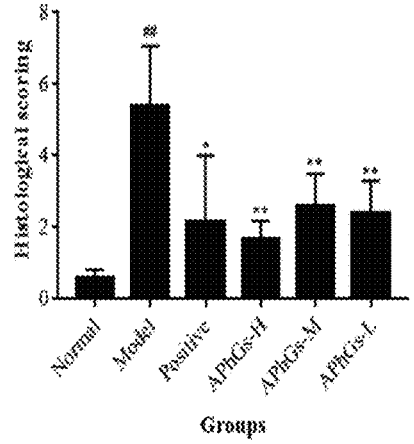
FIG. 4B is the pathological tissue section scoring diagram (compared with the normal group ##P<0.01; compared with the model group *P<0.05, **P<0.01).

The liver tissue of the mice in each experimental group were stained and photographed for analysis. It was found that the liver tissue cells of the mice in the normal group were intact with no pathological changes (FIG. 4). In the model group, the hepatocytes of the mice showed cytoplasmic porosity, and balloon-like degeneration of hepatocytes, cell necrosis, red staining of cytoplasm, and inflammatory cell infiltration were observed around the veins. The liver lesion of the mice in the APhGs-H group was ameliorated, and the score for liver injury was decreased. It showed that phenylethanoid glycoside extract could inhibit liver injury induced by $CCl_4$.

3 Conclusions

The pharmacodynamic results of APhGs on $CCl_4$-induced liver injury in mice showed that the early administration of APhGs could reduce the levels of $CCl_4$-induced mouse serum biochemical indexes, ALT and AST, increase SOD activities in serum and liver tissue, and inhibit the production of lipid peroxidation product MDA. Observation of pathological sections demonstrated that APhGs had a significant amelioration effect on liver lesions in mice. It could be concluded that the phenylethanoid glycoside extract had anti-liver injury effects.

Example 3

Study on the Pharmacodynamics of APhGs on $CCl_4$-Induced L-02 Hepatocyte Damage In Vitro.

1 Experimental Methods

L-02 hepatocytes were provided by the China Center for Type Culture Collection (CCTCC). The L-02 hepatocytes were cultured in a medium containing 1640 complete culture medium and DMEM complete medium with 5% $CO_2$ at a constant temperature (37° C.). The cells were harvested in the exponential growth phase. A suspension of $1\times10^6$ cells/mL was prepared, and then 100 μL of this suspension was added to each well of a 96-well plate with tested medium. The groups were divided into: normal group, negative control group, $CCl_4$ model group, positive group (silybin), and high-, medium-, and low-dosage APhGs groups. After incubation for 24 h, the cells in the experimental group and the positive group were treated with different concentrations of APhGs and silybin. Both the $CCl_4$ model group and the negative control group were added with the same amount of DMSO. Each treatment was repeated five times. After incubation for 15 minutes, all the groups except the normal group were treated with 15 mM $CCl_4$ to induce cell damage. The Cell Counting Kit-8 (CCK-8) method was used for cell viability detection after 24 h.

Preparation of APhGs solution: 2 mg of the APhGs prepared in the present disclosure was dissolved in 200 μL DMSO to prepare a mother liquor of 10 mg/mL. 0.4, 0.2, and 0.1 μL of APhGs mother liquor was added to 100 μL of medium to provide final concentrations of 40, 20, and 10 μg/mL, respectively. Preparation of silybin solution: 2 mg of silybin was dissolved in 400 μL of DMSO to prepare a 5 mg/mL mother liquor. 0.4 μL of silybin mother liquor was added to 100 μL of medium to provide a final concentration of 20 μg/mL.

Determination of cell viability: 10 μL of CCK8 was added to each well to incubate at 37° C. for 2 h. The culture plates were measured with a microplate reader to obtain the absorbances at 450 nm. The cell viability values were calculated by the following formula:

$$\text{Cell viability (\%)} = (OD_{sample} - OD_{blank}) \times 100 / (OD_{control} - OD_{blank})$$

$OD_{sample}$ was the absorbance of the experimental group, $OD_{control}$ was the absorbance of the negative control group, $OD_{blank}$ was the absorbance of the blank control.

2 Results

The results showed that the cell survival rate of the $CCl_4$ model group was 24.22±0.33%. The cell survival rate of the 20 μg/mL APhGs was 34.38±4.90%, which was similar to the survival rate of the positive drug group (35.92±2.15%) at the same concentration.

3 Conclusions

The APhGs could increase the survival rate of L-02 hepatocytes induced by $CCl_4$. It was confirmed that the phenylethanoid glycoside extract could prevent liver injury.

INDUSTRIAL APPLICABILITY

The present application discloses the use of phenylethanoid glycoside extract from *A. ilicifolius* L. in anti-liver injury use for the first time. The preparation method of phenylethanoid glycoside extract from *A. ilicifolius* L. in the present disclosure is simple, and easy to operate, with high production efficiency. The anti-liver injury effect of the phenylethanoid glycoside extract from *A. ilicifolius* L. is significant, and which could restore normal biochemical indexes in the mouse serum and liver tissue, ameliorate the liver diseases of the mice, and increase the survival rates of liver cells in vitro. The present disclosure provides a new direction for the prevention and treatment of liver injury.

The invention claimed is:

1. A phenylethanoid glycoside extract, wherein the phenylethanoid glycoside extract comprises at least four compounds of acteoside, isocrenatoside, isoacteoside and p-coumaric acid, and the phenylethanoid glycoside extract is prepared by a method comprising following steps:

pulverizing dried whole plant *Acanthus ilicifolius* L. and passing through a 20-30 mesh sieve to obtain *Acanthus ilicifolius* L. powder, adding a 50%-95% ethanol solution whose mass is 8-20 times of the powder, soaking for 1-3 h and then extracting under reflux for 2-4 h, filtering and collecting an extract of the powder, and then extracting a filter residue under reflux for 1.5-2 h with 50%-95% ethanol solution whose mass is 8-10 times of the filter residue and collecting an extract of the filter residue, combining the extract of the powder and the extract of the filter residue, concentrating and subjecting to macroporous resin column chromatography, eluting successively by 10%, 30% and 50% ethanol solutions for four column volumes, respectively, collecting a fraction eluted by the 50% ethanol solution and drying to obtain the phenylethanoid glycoside extract, wherein the percentages of ethanol solutions are all volume percentages.

2. The phenylethanoid glycoside extract of claim 1, wherein a content of phenylethanoid glycoside compounds in the phenylethanoid glycoside extract is more than 70 wt %.

3. The phenylethanoid glycoside extract of claim 1, wherein a content of phenylethanoid glycoside compounds in the phenylethanoid glycoside extract is 73.78±2.00 wt %.

4. The phenylethanoid glycoside extract of claim 1, wherein a stationary phase of the macroporous resin column chromatography is D101 or AB-8 macroporous resin.

5. A method for increasing activity of superoxide dismutase (SOD) in a subject, comprising administering an effective dose of a phenylethanoid glycoside extract, wherein the phenylethanoid glycoside extract comprises at least four compounds of acteoside, isocrenatoside, isoacteoside and p-coumaric acid, and the phenylethanoid glycoside extract is prepared by a method comprising following steps:

pulverizing dried whole plant *Acanthus ilicifolius* L. and passing through a 20-30 mesh sieve to obtain *Acanthus ilicifolius* L. powder, adding a 50%-95% ethanol solution whose mass is 8-20 times of the powder, soaking for 1-3 h and then extracting under reflux for 2-4 h, filtering and collecting an extract of the powder, and then extracting a filter residue under reflux for 1.5-2 h with 50%-95% ethanol solution whose mass is 8-10 times of the filter residue and collecting an extract of the filter residue, combining the extract of the powder and the extract of the filter residue, concentrating and subjecting to macroporous resin column chromatography, eluting successively by 10%, 30% and 50% ethanol solutions for four column volumes, respectively, collecting a fraction eluted by the 50% ethanol solution and drying to obtain the phenylethanoid glycoside extract, wherein the percentages of ethanol solutions are all volume percentages.

6. The method of claim 5, wherein a content of phenylethanoid glycoside compounds in the phenylethanoid glycoside extract is more than 70 wt %.

7. The method of claim 5, wherein a content of phenethanol glycoside compounds in the phenylethanoid glycoside extract is 73.78±2.00 wt %.

8. The method of claim 5, wherein the stationary phase of the macroporous resin column chromatography is D101 or AB-8 macroporous resin.

9. A method for reducing a level of lipid peroxide malondialdehyde (MDA) in a subject, comprising administering an effective dose of a phenylethanoid glycoside extract, wherein the phenylethanoid glycoside extract comprises at least four compounds of acteoside, isocrenatoside, isoacteoside and p-coumaric acid, and the phenylethanoid glycoside extract is prepared by a method comprising following steps:

pulverizing dried whole plant *Acanthus ilicifolius* L. and passing through a 20-30 mesh sieve to obtain *Acanthus ilicifolius* L. powder, adding a 50%-95% ethanol solution whose mass is 8-20 times of the powder, soaking for 1-3 h and then extracting under reflux for 2-4 h, filtering and collecting an extract of the powder, and then extracting a filter residue under reflux for 1.5-2 h with 50%-95% ethanol solution whose mass is 8-10 times of the filter residue and collecting an extract of the filter residue, combining the extract of the powder and the extract of the filter residue, concentrating and subjecting to macroporous resin column chromatography, eluting successively by 10%, 30% and 50% ethanol solutions for four column volumes, respectively, collecting a fraction eluted by the 50% ethanol solution and drying to obtain the phenylethanoid glycoside extract, wherein the percentages of ethanol solutions are all volume percentages.

10. The method of claim 9, wherein a content of phenethanol glycoside compounds in the phenylethanoid glycoside extract is more than 70 wt %.

11. The method of claim 9, wherein a content of phenylethanoid glycoside compounds in the phenylethanoid glycoside extract is 73.78±2.00 wt %.

12. The method according to claim 9, wherein the stationary phase of the macroporous resin column chromatography is D101 or AB-8 macroporous resin.

* * * * *